US006182341B1

(12) United States Patent
Talbot et al.

(10) Patent No.: US 6,182,341 B1
(45) Date of Patent: *Feb. 6, 2001

(54) METHOD OF MANUFACTURING AN IMPROVED COUPLING OF ACOUSTIC WINDOW AND LENS FOR MEDICAL ULTRASOUND TRANSDUCERS

(75) Inventors: Jim Talbot, Menlo Park; Oren Shelley; Sevig Ayter, both of Cupertino; Marilou F. Camacho, Union City; John William Sliwa, Jr., Palo Alto; Walter T. Wilser, Cupertino, all of CA (US)

(73) Assignee: Acuson Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/188,762

(22) Filed: Nov. 9, 1998

Related U.S. Application Data

(62) Division of application No. 08/480,675, filed on Jun. 7, 1995, now Pat. No. 5,834,687.

(51) Int. Cl.[7] .................................................. H01L 41/00
(52) U.S. Cl. ................... 29/25.35; 174/35 MS; 310/336; 600/459
(58) Field of Search .......................... 29/25.35; 361/816, 361/818, 800; 428/418; 174/35 R, 35 MS, 35 TS, 52.1; 600/459; 310/334–336

(56) References Cited

U.S. PATENT DOCUMENTS 4,651,310 * 3/1987 Kaneko et al. ...................... 367/140
5,327,008 * 7/1994 Djennas et al. ..................... 257/666

* cited by examiner

Primary Examiner—Carl E. Hall
(74) Attorney, Agent, or Firm—Brinks Hofer Gilson Lione (57) ABSTRACT

A method for improving the coupling of an acoustic window or lens to a RFI shield by modifying the surface of the shield to promote adhesion. The surface of the shield can be chemically modified with an epoxy and/or mechanically modified by creating an unsmooth top surface.

9 Claims, 4 Drawing Sheets

METHOD OF MANUFACTURING AN IMPROVED COUPLING OF ACOUSTIC WINDOW AND LENS FOR MEDICAL ULTRASOUND TRANSDUCERS

This application is a division of application Ser. No. 08/480,675, filed Jun. 7, 1995, now U.S. Pat. No. 5,834,687.

FIELD OF THE INVENTION

This invention relates to transducers and more particularly to broadband phased array transducers for use in the medical diagnostic field.

Ultrasound machines are often used for observing organs in the human body. Typically, these machines incorporate transducer arrays for converting electrical signals into pressure waves and vice versa. Generally, the transducer array is in the form of a hand-held probe which may be adjusted in position while contacting the body to direct the ultrasound beam to the region of interest. Transducer arrays may have, for example, 128 phased transducer elements for generating an ultrasound beam.

An electrode is placed at the front and rear portion of the transducer elements for individually exciting each element. The pressure waves generated by the transducer elements are directed toward the object to be observed, such as the heart of a patient being examined. Each time the pressure wave confronts tissue having different acoustic characteristics, a portion of the ultrasound wave is reflected backward. The array of transducers may then convert the reflected pressure waves into corresponding electrical signals. An example of a phased array acoustic imaging system is described in U.S. Pat. No. 4,550,607 granted Nov. 5, 1985 to Maslak et al. and is incorporated herein by reference. That patent illustrates circuitry for focusing the incoming signals received by the transducer array in order to produce an image on the display screen.

The elevation focus of most phased array transducers can generally be categorized as lens focused or mechanically focused. In the case of lens focused transducer arrays the emitting surface of the array is flat in the elevation direction and a material, the lens, is placed between the object to be imaged and the array. The lens material has a lower velocity of sound than the object being imaged for a convex shaped lens surface. The focusing of the ultrasound beam is achieved through the refraction at the lens/object interface. U.S. Pat. Nos. 4,686,408 and 5,163,436 describe lens focused phased array transducers and are specifically incorporated herein by reference.

Mechanically focused transducer arrays utilize a piezoelectric layer and matching layers which have a curved surface which face the object to be imaged. The surface is curved along the elevation direction and forms either a concave or convex structure. U.S. Pat. Nos. 4,184,094 and 4,205,686 described such a mechanically focused transducer array and are hereby specifically incorporated by reference. The curved surface of the top matching layer is then covered by an acoustic window which is usually formed from a low attenuation polymeric material. The polymeric material is considered an acoustic window and provides no focusing of the acoustic beam. Several two part castable polyurethane materials can be used as acoustic windows.

With reference to acoustic windows, it is possible to use polymeric materials with acoustic attenuation as low as 1.0 dB/mm at around 7 MHz and sound velocity very close to that of human body tissue, i.e. about 1,540 m/s. The use of low loss acoustic window materials in combination with a mechanically focused stack results in better depth penetration of the acoustic beam into the human body being imaged. With reference to the lens structure previously described, the lens material is much more attenuative than the acoustic window material, i.e. around 5.5 dB/mm at about 7 MHz, with velocity of sound far below that of water or the human body. Lower velocity materials such as these provide focusing of the acoustic beam in the elevation plane. Typically silicone RTV materials are used as these later lens materials.

Often a radio frequency interference (RFI) shield is provided underneath the lens or window. The RFI shield is used to reduce electromagnetic interference caused by the hospital or clinical environment which would produce noise in the ultrasound image or vice versa. There are various techniques for employing an RFI shield. One form of shield includes a polymeric shield substructure that has been sputtered with a thin metal. Often, the metal of choice is gold because gold has good conductivity and relative stability in the presence of various deleterious disinfecting solutions used by hospitals and clinics to disinfect the transducer between patient use.

A disadvantage associated with polymeric materials used to form windows or lenses is that they all absorb liquids to some extent, polyurethanes more so than silicones. The gold of the RFI shield acts as a relatively inert barrier to further ingress of these solutions that might occur as a result of repeated soaking of the transducer between patient uses to achieve a satisfactory level of disinfection or sterilization.

It is often difficult to achieve adequate adhesion between the window or lens material and the typically smooth metal surface of the RFI shield. In addition, it is often difficult to maintain adequate adhesion throughout the lifetime of the probe due to the repeated soakings of the transducer probe in disinfecting solution between patients. Transducer typically may be subjected to over 1,000 disinfecting cycles in a year, each cycle lasting anywhere from about 20 to 45 minutes. If the transducer probe is subject to sterilization, the soak time may be as long as 10 hours. The eventual ingress and diffusion of the disinfecting solutions through the window or lens of the transducer causes delamination of the window or lens from the underlying RFI shield. Delamination of this type results in poor image quality and typically the transducer must be returned to the manufacturer.

It is thus desirable to provide a method for optimizing the adhesion of the window or lens material to the underlying RFI shield so that repeated disinfection or sterilization cycles do not compromise the integrity of the transducer structure.

It is also desirable to promote the adhesion between the window or lens material with the underlying shield in a simple and inexpensive manner.

SUMMARY OF THE INVENTION

According to a first aspect of the present invention there is provided a shield for reducing the impact of radio frequency interference for an ultrasound transducer having a shield substructure including a polymeric film, a layer of metal disposed on the polymeric film and a layer of epoxy material coating the layer of metal.

According to a second aspect of the present invention there is provided a method of manufacturing a shield for reducing the influence of radio frequency interference for an ultrasound transducer. The method includes providing an acoustic stack, providing a shield substructure over a portion of the acoustic stack so that a top surface of the shield substructure faces an object to be imaged and treating the top surface of the shield substructure to promote adhesion with a covering.

DETAILED DESCRIPTION OF THE PRESENTLY PREFERRED EMBODIMENTS

Figure 1:
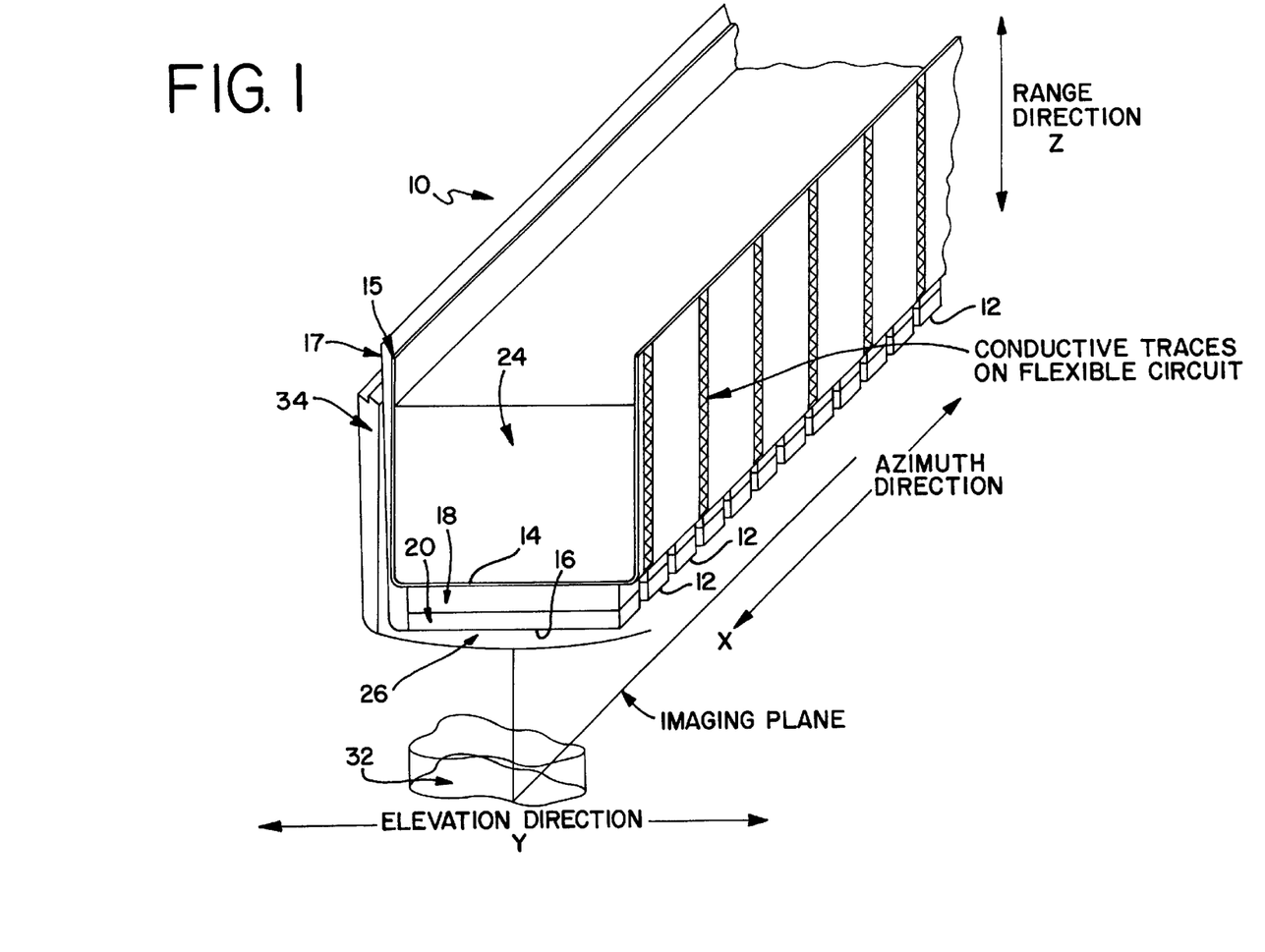
FIG. 1 illustrates a prior art transducer array 10 for generating an ultrasound beam.

FIG. 1 illustrates generally a transducer array 10 for generating an ultrasound beam. Typically, such an array may have 128 transducer elements 12 in the azimuthal direction. Adapted from radar terminology, the x, y, and z directions are referred to as the azimuthal, elevation, and range directions, respectively.

Each transducer element 12, typically rectangular in cross-section, may comprise a first electrode 14, a second electrode 16 and a piezoelectric layer 18. In addition, one or more acoustic matching layers 20 may be disposed over the piezoelectric layer 18 to increase the efficiency of the sound energy transfer to the external medium. The electrode 14 for a given transducer element 12 may be part of a flexible circuit 15 for providing the hot wire or excitation signal to the piezoelectric layer 18. Electrode 16 for a given transducer element may be connected to a ground shield return 17. To further increase performance, the piezoelectric layer 18 may be plated or metalized on its top and bottom surfaces and the matching layer 20 may also be plated or metalized on all surfaces so that electrode 16 which is in physical contact with the matching layer 20 is electrically coupled to a surface of the piezoelectric layer 18 by the plating.

The transducer elements 12 are disposed on a support or backing block 24. The backing block 24 may be highly attenuative such that ultrasound energy radiated in its direction (i.e., away from an object 32 of interest) is substantially absorbed. In addition, a mechanical lens 26 may be placed on the matching layer 20 to help confine the generated beam in the elevationrange plane and focus the ultrasound energy to a clinically useful depth in the body. Alternately the piezoelectric layer 18 may have a curved surface facing the object to be imaged and a low loss acoustic window may be disposed over the piezoelectric layer such as the transducer array described in U.S. Pat. No. 5,415,175 granted May 16, 1995 to Hanafy et al. which is specifically incorporated herein by reference.

Alternatively, the piezoelectric layer 18 may have a plano-concave shape such as that disclosed in U.S. Pat. No. 5,415,175 to Hanafy et al. issued May 16, 1995 which is specifically incorporated herein by reference. The concave surface faces the object 32 to be imaged.

The transducer array 10 may be placed in a nose piece 34 which houses the array. Examples of prior art transducer structures are disclosed in Charles S. DeSilets, *Transducer Arrays Suitable for Acoustic Imaging*, Ph.D. Thesis, Stanford University (1978) and Alan R. Selfridge, *Design and Fabrication of Ultrasonic Transducers and Transducer Arrays*, Ph.D. Thesis, Stanford University (1982).

The materials used to form the various parts of the transducer array are commonly used in the transducer area. The backing block 24 and acoustic matching layers 20 can be manufactured using common epoxies or urethane as can be purchased from Hysol of Pittsburgh, Calif., for example. Fillers such as aluminum oxide may also be used. The materials can be optimized to reduce the reflection of the acoustic energy at the layer interfaces. In a preferred embodiment, the backing block 24 is formed of an acoustic absorbing material which absorbs spurious and unwanted acoustic energy. In a preferred embodiment, the backing block may be formed of a filled epoxy comprising Dow Corning's part number DER 332 treated with Dow Corning's curing agent DEH 24 and has an aluminum oxide filler.

Individual elements 12 can be electrically excited by electrodes 14 and 16 with different amplitude and phase characteristics to steer and focus the ultrasound beam in the azimuthal-range plane. An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce a focused image on the display screen. When an electrical signal is imposed across the piezoelectric layer 18, the thickness of the layer momentarily changes slightly. This property is used to generate sound from electrical energy. Conversely, electrical signals are generated across the electrodes in contact with the piezoelectric layer 18 in response to thickness changes that have been imposed mechanically.

The pressure waves generated by the transducer elements 12 are directed toward an object 32 to be observed, such as the heart of a patient. Each time the pressure wave confronts tissue having different acoustic characteristics, a portion of the wave is reflected backward. The array of transducers may then convert the reflected pressure waves into corresponding electrical signals.

For the transducer shown in FIG. 1 the beam is said to be mechanically focused in the elevation direction by mechanical lens 26. The focusing of the beam in the azimuthal direction is done electronically by controlling the timing of the transmissions and receptions of each transducer element. This may be accomplished by introducing appropriate phase delays in the firing and switching signals.

Reflected energy from a particular location in the image plane is collected by the transducer elements. The resultant electronic signals from individual transducer elements are individually detected and reinforced by the focusing delays. Extensive processing of such data from the entire image plane is done to generate an image of the object. Such an image is typically displayed on a CRT monitor at 10 to 30 frames/second.

Figure 2:
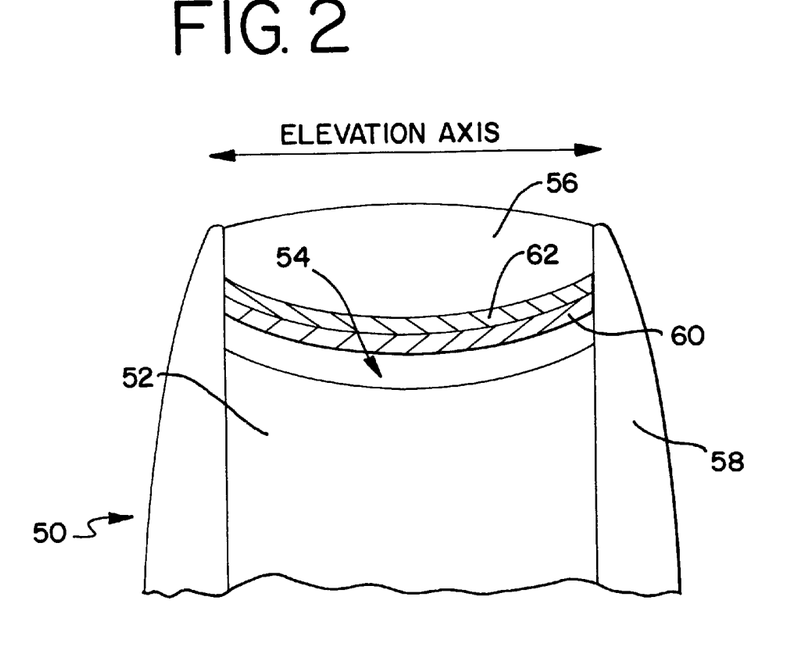
FIG. 2 illustrates a cross-sectional view of a transducer array according to a first preferred embodiment of the present invention.

FIG. 2 illustrates a cross-sectional view of a transducer array 50 according to a first preferred embodiment of the present invention. The cross-section is taken along the elevation direction. The array 50 includes an acoustic stack 52, an RFI shield 54 and a low loss acoustic window 56. The acoustic stack 52 includes a backing block, signal and ground flex circuits, piezoelectric crystal and, if desired, acoustic matching layers such as that shown in FIG. 1. The details of the acoustic stack in FIGS. 2, 4–9 are not illustrated. In a preferred embodiment a plano-concave piezoelectric layer is used, thus the top surface of the acoustic stack 52 is illustrated as concave in shape. A nose piece 58 surrounds the acoustic stack 52, RFI shield 54 and the sides of the low loss acoustic window 56. The RFI shield 54 in this preferred embodiment includes a polymeric shield substructure having at least one layer of refractory metal thereon. The RFI shield structure will be described in greater detail with reference to FIG. 3. In a preferred embodiment, to promote the adhesion between the low loss acoustic window material 56 and the RFI shield 54, the top surface of the RFI shield 54 is modified. In this preferred embodiment the top surface of the RFI shield 54 is treated with a primer 60, preferably a liquid organofunctional silane (or titanate or zirconate) primer such as DOW CORNING 1200 or CHEMLOK AP131 commercially available from Lord Company of Erie, Pa. Then an epoxy seed layer 62 is deposited over the primed top surface of the shield 54. Preferably the epoxy seed layer 62 is no more than about 5 microns thick. Once the epoxy seed layer 62 is cured, the low loss polyurethane window material 56 is cast directly on top of the epoxy layer 62.

In a preferred embodiment, the window material is a low loss polyurethane such as U-2008 manufactured by Castall Inc. of Weymouth Industrial Park, East Weymouth, Mass. The epoxy seed layer 62 is preferably a premixed, frozen adhesive such as Hysol RE2039 commercially available from Dexter-Hysol of Los Angeles, Calif. The nose piece 58 is preferably formed from a rigid engineering thermoplastic such as RADEL manufactured by Amoco.

In an alternate embodiment, the top surface of the RFI shield 54 may not be primed with a liquid silane primer although this has been shown to promote the adhesion of the window material 56 to the RFI shield 54. The metal of the RFI shield 54 may be selected from the group including gold, titanium, chromium or alloys thereof. The polymeric shield substructure may be selected from the group including polyimide, polyester, polyurethane, or PEN. The low loss window may be a polymer selected from the group consisting of MDI polyester based polyurethane, MDI polyether based polyurethane, TDI polyester based polyurethane, TDI polyether based polyurethane, polybutadiene and polyether/polyester polyurethane copolymer.

The reliability of the resulting bond between the window material 56 and the RFI shield 54 has been demonstrated using standard lap shear coupons. The lap shear coupons simulate the structure shown in FIG. 2 and were shown to withstand a 30 day soak in the following commercially available liquid disinfectants such as CIDEX, GIGASEPT ff, ENDOSPOR, MATAR and VIRKON and still retained a bond strength of no less than 60% of the strength measured on unsoaked control coupons of a similar structure.

Figure 3:
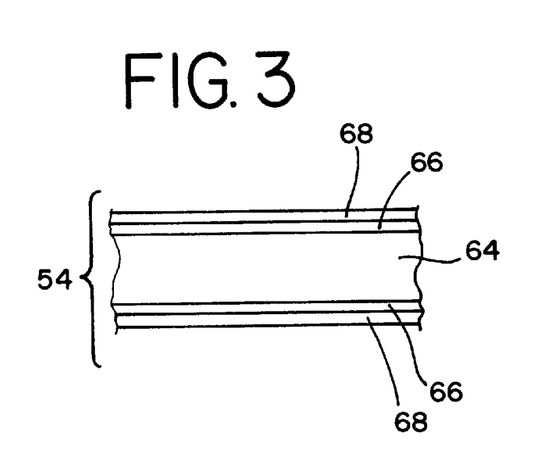
FIG. 3 illustrates a portion of the RFI shield shown in FIG. 2 taken along the elevation direction.

FIG. 3 illustrates a portion of the RFI shield 54 shown in FIG. 2 taken along the elevation direction. In a preferred embodiment, the shield 54 includes a shield substructure 64, a seed layer 66 on both sides of the shield substructure 64 and a layer of metal 68 over the seed layers 66. In a preferred embodiment the shield substructure 64 may be formed of polyimide, the adhesion layer 66 is preferably formed of titanium and the metal 68 is gold. The shield substructure 64 is first coated with the titanium seed layer 66 and then the metal layer 68 is deposited thereon preferably by sputtering. The titanium seed layers 66 underneath the layer of refractory metal help promote the integrity of the shield.

Figure 4:
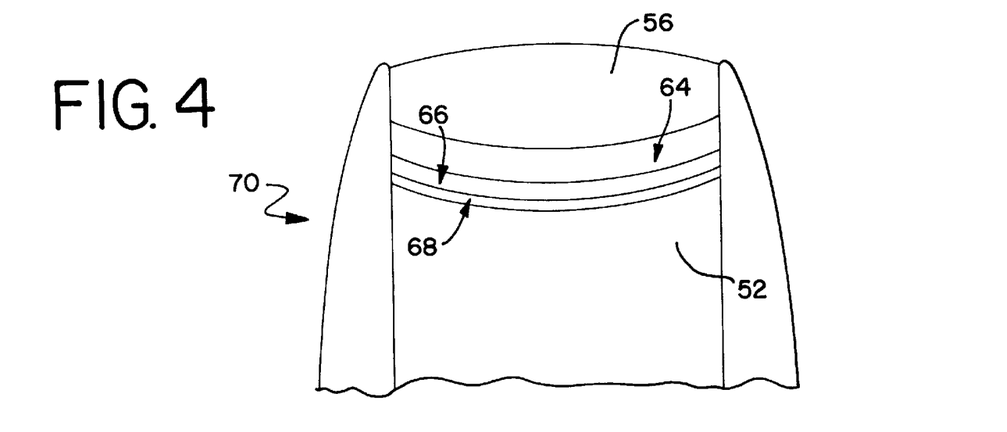
FIG. 4 illustrates a cross-sectional view of a transducer array according to a second preferred embodiment of the present invention.

FIG. 4 illustrates a cross-sectional view of a transducer array 70 according to a second preferred embodiment of the present invention. The cross-section is taken along the elevation direction. The transducer arrays in the following figures are similar to that already described in FIG. 2 and thus the same reference numerals will be used to describe similar elements. This preferred embodiment is similar to that shown in FIG. 2 except that the layer of refractory metal on the top of the RFI shield 54 has been removed and the low loss polyurethane window material 56 is directly bonded to the polymeric shield substructure 54. The top surface of the shield substructure 64 may be treated with an epoxy. The resulting bond strength between the window material 56 and the polymeric shield structure 64 is significantly stronger than the bond between the window material and the smooth surface of a refractory metal. The layer of metal needed for the RFI shield 54 is located on the underside of the polymer shield substructure 64 as illustrated.

Figure 5:
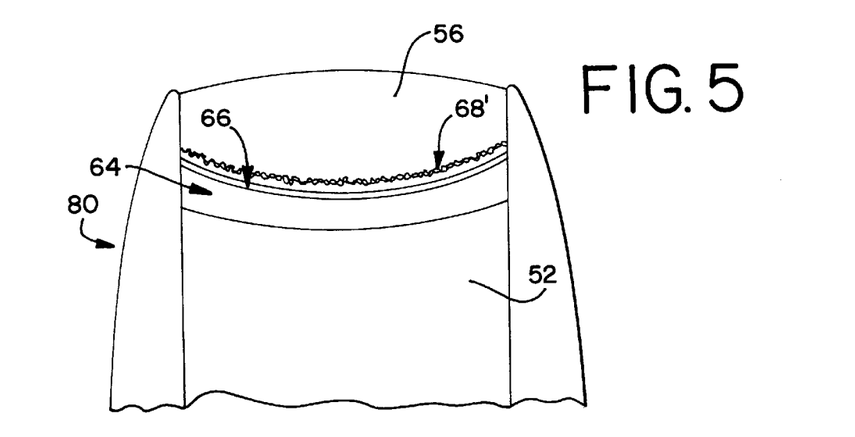
FIG. 5 illustrates a cross-sectional view of a transducer array according to a third preferred embodiment of the present invention. The cross-section is taken along the elevation direction.
Figure 6:
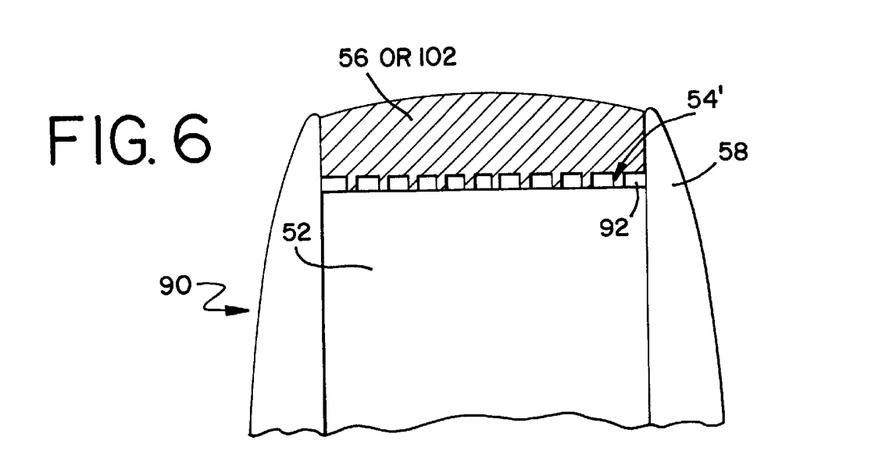
FIG. 6 illustrates a cross-sectional view of a transducer array according to a fourth preferred embodiment of the present invention.

With reference to FIGS. 2–4, the top surface of the RFI shield is modified chemically. It is also possible to mechanically modify the top surface of the RFI shield to promote adhesion between the window material and the RFI shield. FIGS. 5 and 6 illustrate two alternate embodiments for mechanically modifying the top surface of the RFI shield.

FIG. 5 illustrates a cross-sectional view of a transducer array 80 according to a third preferred embodiment of the present invention. The cross-section is taken along the elevation direction. In this preferred embodiment, the top surface 82 of the layer of refractory metal 68' is not smooth. The unsmooth top surface allows for mechanical bonding between the window material 56 and the refractory metal 68'. In addition to mechanical modification, the top surface of the refractory metal may be chemically modified as well as shown in FIG. 2 to provide chemical bonding as well as mechanical bonding. Various techniques may be used to provide an unsmooth top surface of the refractory metal including plasma etching the shield substructure after it has been metalized or alternatively, before the shield substructure is metalized, using a rough polymeric shield material such as polyimide so that the layer of refractory metal will conform to this unsmooth surface. Alternatively, holes, slots or patterns may be formed in the polymeric shield material to create an unsmooth surface.

FIG. 6 illustrates a cross-sectional view of a transducer array 90 according to a fourth preferred embodiment of the present invention. The cross-section is taken along the elevation direction. In this preferred embodiment either a window material 56 or lens material 102 may be cast on the RFI shield. In this preferred embodiment, a plurality of holes 92 have been drilled in top surface of the RFI shield 54'. The window material or lens material can then be cast on the RFI shield. The window or lens material fills these holes which serve as anchors to mechanically enhance the adhesion between the window or lens material and the metal of the RFI shield. The holes may be drilled with a laser or they may be precisely located using standard photolithography and dry or wet etching techniques. The size of the holes and their spacing must be small compared to the acoustic wavelength in the transducer, preferably in the submicron range.

The embodiments shown in FIGS. 5 and 6 thus provide a mechanical bond between the window or lens material and the RFI shield. The mechanical bond may be enhanced by also providing a chemical bond as shown in FIGS. 2 and 4.

Figure 7:
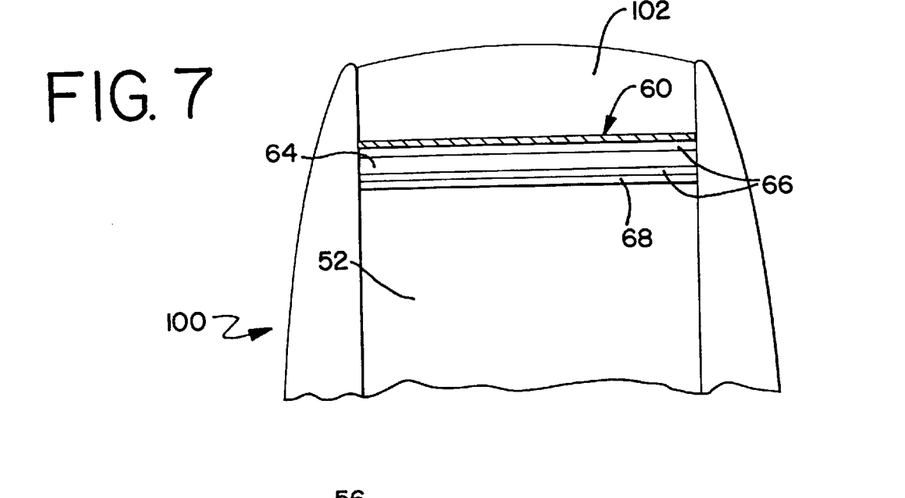
FIG. 7 illustrates a cross-sectional view of a transducer array according to a fifth preferred embodiment of the present invention.

FIG. 7 illustrates a cross-sectional view of a transducer array according 100 to a fifth preferred embodiment of the present invention. The cross-section is taken along the elevation direction. In this preferred embodiment a RTV silicone focusing lens 102 is used in conjunction with a titanium 66 coated polymeric shield substructure 64 has been primed with a liquid organofunctional silane primer 60. The thickness of the titanium 66 can be as thin as a few hundred Angstroms. In an alternate embodiment, the shield substructure 64 may be provided with a layer of refractory metal which has been plasma etched or UV Ozone cleaned prior to casting the RTV silicone to optimize the adhesion between the RFI shield and the lens material. In a preferred embodiment, the polymeric shield substructure is formed of polyimide or polyester which has been first primed with a liquid organofunctional silane primer such as DOW CORNING 1200.

The bond strength resulting from the selection of materials shown in FIG. 7 has been analytically tested. The resulting bond strength of an RTV silicone such as DOW CORNING Q8008 to a titanium coated shield which has been primed with DOW CORNING liquid silane primer 1200 is able to withstand a prolonged soak for 30 days in a variety of liquid disinfectants. This bond strength was measured by assembling lap shear coupons similar to those previously described. For the testing, the RTV silicone material is bonded between two rigid coupons. The lower coupon is a solid aluminum coupon that has been sputtered with titanium to simulate the layer of refractory metal of the RFI shield. The upper coupon is a stainless steel coupon with a mesh pattern that allows penetration of the liquid disinfectant in which the coupon is soaked to ingress into the silicone RTV. The lower coupon's titanium sputtered surface is cleaned in a manner that would be used in the manufacturing process to clean a typical RFI shield, i.e., mild aqueous detergent clean followed by a deionized water rinse and low temperature over dry. Following this cleaning the titanium is primed preferably using DOW CORNING 1200 liquid silane primer similar to the process used on an actual RFI shield top surface metalization. Coupons prepared in this manner have been soaked in various liquid disinfectants typically used in hospitals and clinics for up to 30 days and then pulled apart using an Instron tensile instrument. Adhesive bond strengths between the RTV silicone lens material and the titanium on the lower coupons have been shown to exceed 400 psi on those coupons which have been soaked for 30 days in the following commercially available disinfectants: CIDEX, ENGARDE, GIGASEPT, GIGASEPT ff, KORSOLEX, SEKUSEPT EXTRA, and VIRKON.

Figure 8:
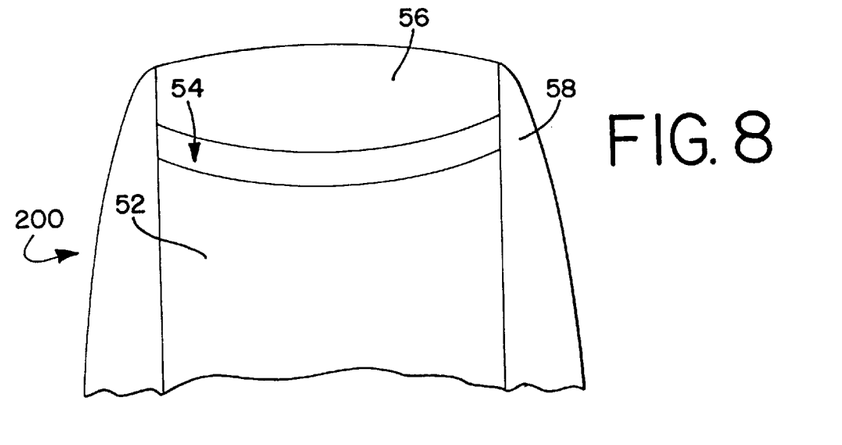
FIG. 8 illustrates a cross-sectional view of a transducer array according to a sixth preferred embodiment of the present invention.

FIG. 8 illustrates a cross-sectional view of a transducer array 200 according to a sixth preferred embodiment of the present invention. The cross-section is taken along the elevation direction. In this preferred embodiment, a low loss polymeric material 56 such as polybutadiene is compression molded directly onto the housing. In a preferred embodiment the housing is made of a rigid high temperature engineering thermoplastic such as RADEL manufactured by Amoco. The acoustic stack 52 is inserted into the nose piece 58 after the polymeric window 56 has been compression molded onto the patient facing end of the transducer. The RFI shield 54 may be prepared in any one of the numerous ways already discussed to optimize the adhesion between the RFI shield and the polymeric window. For example, the layer of refractory metal of the RFI shield could be plasma etched, UV Ozone cleaned or primed with a liquid silane primer prior to coating with an epoxy adhesive such as Hysol's RE2039.

The use of a compression molded polymer such as polybutadiene provides several advantages. The class of rubbers which can be compression molded are very tough, i.e. they have a high tear strength, and are chemically resistant to prolonged soaks in typical liquid disinfectants. In addition, the process of compression molding directly onto the nose piece results in an environmental seal around the entire nose piece perimeter. Such a seal deters the penetration of disinfectants and coupling gels around the sides of the polymeric window which might eventually compromise the adhesion of the window to the underlying RFI shield.

The compression molded polymer described above could also be manufactured as a premolded structure. This premolded structure could be attached to the RFI shield or acoustic stack using adhesives such as Hysol's RE2039. Details could be manufactured on the inside of the nose piece housing to capture this premolded structure so that its location is consistently assured.

Figure 9:
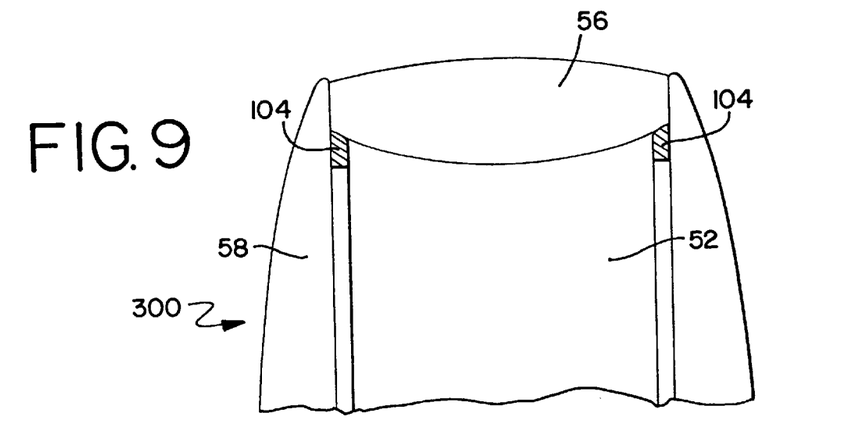
FIG. 9 illustrates a cross-sectional view of a transducer array according to a seventh preferred embodiment of the present invention.

FIG. 9 illustrates a cross-sectional view of a transducer array 300 according to a seventh preferred embodiment of the present invention. The cross-section is taken along the elevation direction. Liquid disinfectants may also seep into the transducer between the nose piece and acoustic stack. In a preferred embodiment a chemical barrier in the form of an RTV silicone bead 104 is located between the nose piece 58 and the acoustic stack 52. The bead 104 encircles the perimeter of the acoustic stack 52. The bead minimizes the ingress of disinfectants or other chemicals used to clear or image ultrasound transducers such as coupling gels around the edges of the acoustic stack. The bead 104 may also be used in conjunction with the previously described embodiments.

It is to be understood that the forms of the invention described herewith are to be taken as preferred examples and that various changes in the shape, size and arrangement of parts may be resorted to, without departing from the spirit of the invention or scope of the claims.

What is claimed is:

1. A method of manufacturing an ultrasound transducer having a shield for reducing radio frequency interference on the ultrasound transducer, the method comprising the steps of:

providing an acoustic stack;

providing a shield substructure over a portion of said acoustic stack so that a top surface of said shield substructure faces an object to be imaged;

depositing a layer of epoxy on said top surface, said epoxy layer promoting adhesion with an adjacent covering to be subsequently added;

curing said layer of epoxy prior to providing the adjacent covering; and providing the adjacent covering directly onto the cured epoxy layer adjacent to said top surface of said shield substructure.

2. A method according to claim 1 further comprising the step of priming said top of said shield substructure with a liquid silane primer prior to depositing said layer of epoxy.

3. A method according to claim 1 wherein said covering is a low loss acoustic window.

4. A method according to claim 1 wherein said covering is a RTV silicone lens.

5. A method according to claim 1 wherein said shield substructure comprises a metal selected from the group consisting of titanium, chromium, and alloys thereof.

6. A method of manufacturing an ultrasound transducer having a shield for reducing radio frequency interference on the ultrasound transducer, the method comprising the steps of provi ding an acoustic stack;

providing a shield substructure over a portion of said acoustic stack so that a top surface of said shield substructure faces an object to be imaged;

depositing a layer of liquid silane primer on said top surface, said liquid silane layer promoting adhesion with an adjacent covering to be subsequently added; and providing the adjacent covering directly onto the silane layer adjacent to said top surface of said shield substructure.

7. A method according to claim 6 wherein said covering is a low loss acoustic window.

8. A method according to claim 6 wherein said covering is a RTV silicone lens.

9. A method according to claim 6 wherein said shield substructure comprises a metal selected from the group consisting of titanium, chromium, and alloys thereof.

* * * * *

UNITED STATES PATENT AND TRADEMARK OFFICE
CERTIFICATE OF CORRECTION

PATENT NO.    : 6,182,341 B1
DATED         : February 6, 2001
INVENTOR(S)   : Jim Talbot et al.

It is certified that error appears in the above-identified patent and that said Letters Patent is hereby corrected as shown below:

<u>Column 3,</u>
Line 62, delete "elevationrange" and substitute -- elevation-range -- in its place.

<u>Column 5,</u>
Line 14, delete "shield .54" and substitute -- shield 54 -- in its place.

Signed and Sealed this

First Day of April, 2003

JAMES E. ROGAN
*Director of the United States Patent and Trademark Office*